Figure 1:
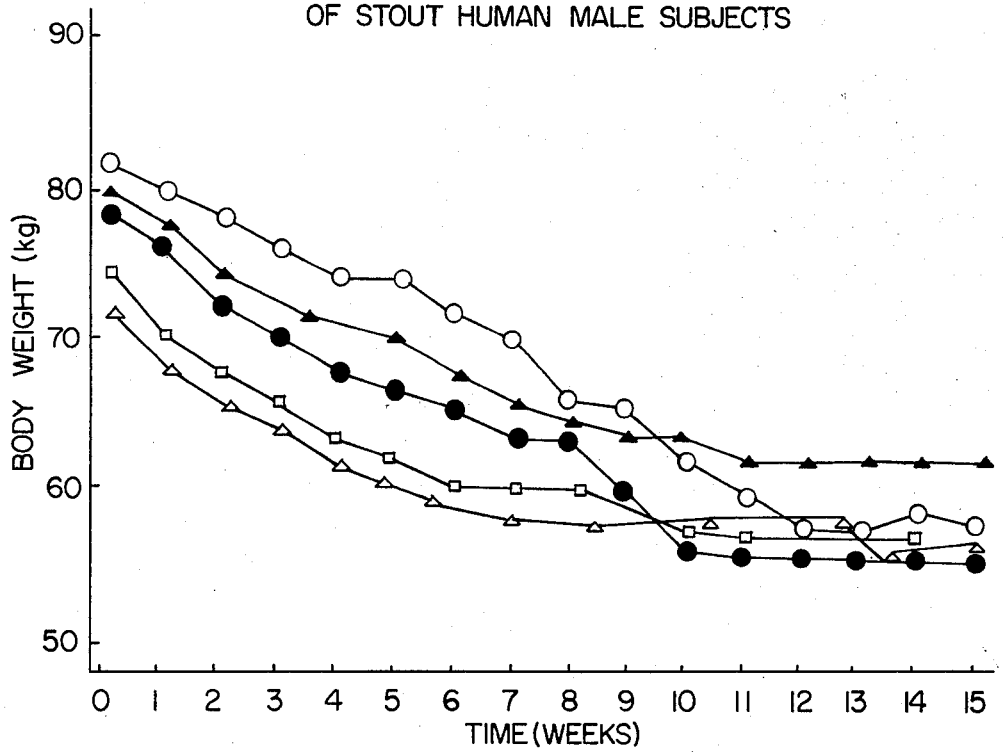

United States Patent [19]
Sugiyama et al.

[11] 3,973,008
[45] Aug. 3, 1976

[54] KONJAC MANNAN

[75] Inventors: Noboru Sugiyama, Tokyo; Hideo Shimahara, Mihara, both of Japan

[73] Assignee: Kabushiki Kaisha Shimizu Manzo Shoten, Japan

[22] Filed: Oct. 9, 1974

[21] Appl. No.: 513,403

Related U.S. Application Data

[63] Continuation-in-part of Ser. No. 179,201, Sept. 9, 1971, Pat. No. 3,856,945.

[30] Foreign Application Priority Data

Dec. 30, 1970 Japan.............................. 45-128288

[52] U.S. Cl............................... 424/195; 424/180
[51] Int. Cl.$^2$................... A61K 35/78; A61K 31/70
[58] Field of Search.................. 260/236.5; 424/195, 424/180; 127/54

[56] References Cited

FOREIGN PATENTS OR APPLICATIONS 2,139,789  12/1973  France.............................. 429/195

*Primary Examiner*—Donald B. Moyer
*Attorney, Agent, or Firm*—William J. Daniel

[57] ABSTRACT

Water-soluble konjac mannan capable of undergoing gelation when heated in an aqueous alkaline solution is obtained by extracting the ground tuber of the konjac plant with water, separating insoluble matter, dialyzing the solids-free liquid against water and then lyophilizing the dialyzed liquid to remove water. This konjac mannan extract has utility for alleviating constipation and reducing weight.

3 Claims, 2 Drawing Figures

EFFECTS OF THE KONJAC MANNAN EXTRACT ON REDUCTION OF BODY WEIGHT OF STOUT HUMAN MALE SUBJECTS

EFFECTS OF THE KONJAC MANNAN EXTRACT ON REDUCTION OF BODY WEIGHT OF STOUT HUMAN FEMALE SUBJECTS

KONJAC MANNAN

This application is a continuation in part of U.S. application Ser. No. 179,201, filed Sept. 9, 1971, now U.S. Pat. No. 3,856,945.

This invention relates to a substantially pure, water-soluble konjac mannan extract and to the use of this konjac mannan to alleviate constipation and reduce weight.

Konjac (Amorphophalus Konjac C. Koch) is a perennial plant belonging to the family Araceae. "Konnyaku", which is made from the tuber of this plant, has been used traditionally for food in Japan for several hundred years. The predominant component of edible konnyaku is a glucomannan called konjac mannan. Edible konnyaku is made from the konjac flour, which is obtained from the dried tuber of this plant.

Several techniques are known in the art for separating konjac mannan from konjac flour. In one, konjac flour is boiled in water, treated with Fehling's solution to convert the mannan to its copper complex, and the latter is decomposed again into the mannan after purification, as disclosed in J. Agr. Chem. Soc. Japan, 6, 991–995 (1930). In another, konjac flour is extracted with water, impurities are removed by precipitating with ethanol and redissolving the precipitate in water several times, and drying the precipitate finally obtained to obtain pure konjac mannan, as disclosed in Bull. Chem. Soc. Japan, 49, 298–322 (1927).

However, konjac mannan obtained by these methods is no longer soluble in water and is not able to form a konjac gel. This is probably due to a kind of denaturation during the processing as has been observed for amylose in alkaline solution, in J. Amer. Chem. Soc., 76, 4595 (1954).

As the result of research on a method of separating konjac mannan in substantially pure form without serious loss of its valuable natural properties, it has been found that a substantially pure, water-soluble konjac mannan can be obtained by extracting the powder of the dried tuber of konjac (Amorphophalus Konjac) with water, removing insoluble materials from the extract, dialyzing it against water and then subjecting the liquid material remaining after such dialysis to lyophilization or freeze-drying.

The water-soluble konjac mannan thus obtained is useful medicinally since it has been found to be effective in alleviating constipation and reducing weight in human beings. Since water-insoluble konjac mannan prepared by conventional methods has no such pharmacological activity, it is quite surprising that the water-soluble konjac mannan prepared by the process described above has such effect.

The object of this invention is thus a method of alleviating constipation or reducing weight in human beings by administering an effective dose of the substantially pure, water-soluble konjac mannan.

These and other objects of this invention will become apparent as the description proceeds.

According to this invention, konjac flour is mixed with water under agitation to make a colloidal solution and the resulting solution is separated from insoluble materials by filtration, centrifugal separation or other suitable procedures, then subjected to dialysis treatment and finally to lyophilization to yield substantially pure konjac mannan.

The konjac flour used as the starting material in this invention is generally prepared either by crushing into fine particles the dried tubers of a plant which belongs to the genus *Colacacia*, preferably Amorphophallus Konjac C. Koch, or by removing starch, fiber, protein, etc., and ethanol-soluble materials from a slurry of ground tubers of the stated type. A commercially available konjac flour sold for the production of edible konnyaku is also useful as a starting material without further preparatory treatment.

A preferred embodiment of the process of this invention involves stirring one volume of the konjac flour with 10–200 volumes of water or grinding one part by weight of raw tuber with 10–100 parts by weight of water, whereby the water-soluble components of the konjac flour, such as konjac mannan, low molecular weight impurities and inorganic salts, are dissolved in the water while the water-insoluble components, such as starch particles, epidermis of tuber and fibrous materials, are precipitated. The insoluble components are readily removed by filtration, centrifugal separation or any of the other known conventional methods. The resulting aqueous colloidal solution is then dialyzed by the usual methods, for example, through a semi-permeable membrane against tap water for 24–48 hours. By this treatment, the water-soluble impurities and inorganic materials contaminating the konjac mannan are removed almost completely.

Finally, removal of water from the resulting solution by lyophilization or freeze-drying under ordinary conditions leaves a substantially pure, water-soluble konjac mannan as a purely white, cotton-like material, which exhibits the natural properties of konjac mannan, i.e. ready solubility in water and capability of forming konnyaku when heated in the form of an aqueous colloidal solution with alkali. In contrast, the konjac mannans prepared by known conventional methods substantially lose these natural properties. Thus, the extracted material of the invention is useful as a food, i.e. in the preparation of konnyaku.

The conditions used for lyophilization are not critical and can vary according to the accepted practice in that art. Temperature in the range of $-75°$ – $0°$ and pressures in the range of $0.001 – 0.1$ mm Hg are acceptible. The lyophilization need not be carried to substantial dryness if the material can be more readily mixed and/or used in the form of a concentrated solution.

The substantially pure, water-soluble konjac mannan extract prepared by the present process is a new product not heretofore identified in the literature and has been found to be effective in reducing weight and/or alleviating constipation, when administered to humans and like warm-blooded animals.

The substantially pure, water-soluble konjac mannan extract may be administered as such, or, if desirable, in the form of a mixture with any carrier conventionally used for internal medicaments. This dose can vary but is generally administered every day within the range from $0.001 – 0.4$ g., per kilogram of body weight, which can be given in several portions if desired.

Useful as pharmaceutically acceptable carriers are water, glucose, lactose, gum arabic, gelatin, mannitol, starch paste, magnesium trisilicate, talc, cone starch, potato starch, keratin, colloidal silica, etc.

The konjac mannan of this invention, or mixture thereof, may be in any desired form, e.g. powder, tablet, capsule, solution, etc. The preparation of the present konjac mannan will be illustrated in more detail by the following procedure.

PREPARATION

A colloidal solution was prepared by dissolving 0.5 g. of a commercially available konjac flour in 100 ml. of water. After standing for 2 hours, the solution was filtered through a 150-mesh nylon filter cloth and then through a glass-filter (3G4) with suction to remove the insoluble materials completely. 50 milliliters of the clear filtrate was packed in a cellophane tube and dialyzed against distilled water for 48 hours. The solution remaining after this treatment was transferred to a well-cleaned Schale and lyophilized at −20°C. and 0.001 mm Hg pressure for about 30 hours in a usual manner. Purely white, cotton-like konjac mannan (0.4 grams) was thus prepared. Anal. Calcd. for $(C_6H_{10}O_5 \cdot \frac{1}{8} H_2O)n$; C, 43,83%; H, 6.28%; Found: D,43,87%; H, 6.22%; N, trace.

The properties of the konjac mannan extract thus obtained are shown in the following table where those of the starting flour and of a purified konjac mannan prepared by a known method are also shown for comparison.

TABLE A

| | Konjac mannon prepared in Preparation | Starting konjac flour (commerically available) | The konjac mannan prepared by a known method * |
|---|---|---|---|
| Solubility in water | soluble | soluble | insoluble |
| Gelability | retained | retained | lost |
| Solubility in 20% NaOH | insoluble | insoluble | soluble |
| Reducing Power | none | present | none |
| Starch-iodine reaction | negative | positive | negative |

* J. Agr. Chem. Soc. Japan, 6, 991–995 (1930)

The konjac mannan extract of this invention is a pure white, light fibrous solid with very high bulk and low density. It has no discernible odor or taste and forms a clear viscous solution or colloidal suspension with water. The fibers can, of course, be shredded or pulverized.

According to conventional dialysis procedure, such as is employed in the practice of the invention, the concentration of the solution is usually within the range of 0.1–1.0% by weight, preferably 0.3–1.0% by weight. The dialysis temperature is generally within the range of 0°–30°C, preferably 3°–10°C. Above about 30°C, the solution tends to undergo decay where the circumstances are suitable for growth of microorganisms. Utilizable as semi-permeable membranes are preferably cellulosic materials, especially cellophane marketed by Visking. Membranes of animal origin, for example, urinary bladder membranes, are generally inappropriate for the purpose of this invention for the reason that their pore size is too large. By employing membranes of vegetable origin such as cellophane, particulate impurities are removed to yield a product having a definite size of molecule. The conditions of the dialysis are not especially critical in practice of this invention, however, and any ranges would be suitable here.

The medical effects of the konjac mannan as well as the safety of this substance for human consumption are demonstrated by the following tests:

Effects on Longevity of Rats and Mice of the Administration of Konjac Mannan Extract The life spans of rats and mice were examined. The life span of gnobiotic mice was about two years, that of conventionally reared ones was about 15 months and that of the animals to which konjac mannan was administered was longer than 2 years. Also, conventionally reared rats survived a year and a half, while those to which konjac mannan was administered survived longer than two years. In animals to which konjac mannan extract was administered, the number of bacteria in the alimentary canal such as stomach, jejunum, and caecum was reduced, and such animals were observed to survive longer than the conventionally reared ones.

Effect of the Administration of Konjac Mannan Extract on Moderate Constipation in Human Females One gram of konjac mannan extract was administered every day for 10 days to 17 women ranging from 20 to 22 in age and suffering from moderate constipation, and its effects on passage, i.e. bowel evacuation, were examined. Two days before administration of the konjac mannan extract, all of the 17 subjects suffered from constipation. On the third day after starting such administration, however, all of them had passage, and thereafter during administration every one had passage every day.

After the administration was stopped, on the following day every one had passage, on the third day thereafter the number of those who had passage decreased to 10 from 17, and a week later all of them were constipated again. Thus, passage was secured during the administration of the pure konjac mannan, but once its administration was stopped, its anticonstipating effect disappeared gradually. The results of this test are summarized below in Table I.

TABLE I

| | | Before administration | During administration | | | After administration | | |
|---|---|---|---|---|---|---|---|---|
| | | 2 days before | the 1st day | the 2nd day | the 3rd day | 1 day after | 3 days after | 7 days after |
| Passage | Present (+) | 0 | 0 | 17 | 17 | 17 | 10 | 0 |
| | Absent (−) | 17 | 17 | 0 | 0 | 0 | 7 | 17 |

Results of the Administration of Konjac Mannan Extract on Constipation of Medium Degree in Human Females Sixteen women ranging from 35 to 40 in age, suffering from constipation of medium degree, were administered one gram of the konjac mannan extract every day for 14 days. The results of such administration are tabulated below, including changes in headache, feeling of fullness, dull feeling and poor appetite which generally accompany constipation, which were determined before and after normal passage, i.e. bowel evacuation, had started by administration of the extract.

TABLE II

|  |  | Before administration | During administration | | | After administration | | |
|---|---|---|---|---|---|---|---|---|
|  |  | 2 days before | the 1st day | the 2nd day | the 3rd day | 1 day after | 3 days after | 7 days after |
| Passage | Present (+) | 0 | 9 | 16 | 16 | 16 | 16 | 9 |
|  | Absent (−) | 16 | 7 | 0 | 0 | 0 | 0 | 7 |
| Headache | Present (+) | 10 | 6 | 0 | 0 | 0 | 1 | 2 |
|  | Absent (−) | 6 | 10 | 16 | 16 | 16 | 15 | 14 |
| Feeling of fullness | Present (+) | 16 | 15 | 0 | 0 | 0 | 1 | 3 |
|  | Absent (−) | 0 | 1 | 16 | 16 | 16 | 15 | 13 |
| Dull feeling | Present (+) | 16 | 12 | 0 | 0 | 0 | 2 | 3 |
|  | Absent (−) | 0 | 4 | 16 | 16 | 16 | 14 | 13 |
| Normal Appetite | Present (+) | 0 | 1 | 8 | 15 | 4 | 3 | 1 |
|  | Absent (−) | 16 | 15 | 8 | 1 | 12 | 13 | 15 |

Two days before starting the administration of the konjac mannan extract, none of the 16 patients had passage, 6 had a headache and 16 felt fullness and dullness and had poor appetite. Accordingly, all of the patients felt unpleasant on account of constipation. As the symptoms of constipation started to weaken through the administration of the konjac mannan extract, headache, feeling of fullness and dull feeling started to disappear. However, on the second day after the administration of the konjac mannan extract had been terminated, all patients returned to their original constipated state.

Effects of the Continuous Administration on Stout Women of the Konjac Mannan Extract for a Prolonged Period of Time The konjac mannan extract was administered in the amount of 1 gram per day for 3 months to 5 stout women ranging from 30 to 35 years of age, who were examined for disorder of the stomach and liver, urinary carbohydrate, urinary protein, body weight and appetite on the 10th day and the end of each of the 1st month, 2nd month and 3rd month from the start of the administration.

No abnormality was found in the stomach, liver and urinary protein. The body weight decreased in each subject, whereas appetite was not found to be influenced. The results are tabulated below in Table III.

TABLE III

|  | 10 days | 1 month | 2 months | 3 months |
|---|---|---|---|---|
| Disorder of Stomach | −[1] | − | − | − |
| Hepatic Disorder | − | − | − | − |
| Urinary Carbohydrates | reduced | reduced | reduced | reduced |
| Urinary Protein | ± | − | − | − |

TABLE III-continued

|  | 10 days | 1 month | 2 months | 3 months |
|---|---|---|---|---|
| Body Weight | reduced | reduced | reduced | reduced |
| Appetite | normal | normal | normal | normal |

[1] + indicates abnormal
− indicates normal

Effect on Fecal Bacteria of the Administration of the Konjac Mannan to Humans

Changes in the number of fecal bacteria in humans due to administration of konjac mannan extract were examined by administering a 10 ml portion of 1% konjac mannan extract solution every day for 10 days to one of each of 7 sets of twins, the other being a control, and thereafter examining a 1 g. sample of feces for content of lactobacilli, enterococci and *Escherichia coli*. As is evident from the following Table IV, the number of lactobacilli was reduced from $10^9$ to $10^5$, that of enterococci from $10^8$ to $10^5$ and that of *Escherichia coli* from $10^9$ to $10^6$.

TABLE IV

|  | Konjac mannan not administered (control) | Konjac mannan administered |
|---|---|---|
| Lactobacilli | $1.2 \times 10^9$ [1] | $5.2 \times 10^5$ [1] |
| Enterococci | $5.8 \times 10^8$ | $6.1 \times 10^5$ |
| Escherichia coli | $1.4 \times 10^9$ | $5.5 \times 10^6$ |

[1] Values are the average of 7 subjects

Effects on Alimentary Bacteria of Administration of Konjac Mannan Extract to Rats Changes in the number of bacteria in various parts of the alimentary canal of rats on administration of the konjac mannan extract were examined by administering the konjac mannan extract to 5 male Wistar rats weighing around 150 g. The number of bacteria found in 1 g. samples of intestinal mucosa in the indicated regions of the alimentary canal is indicated in Table V below:

TABLE V

|  | Stomach | | Jejunum | | Caecum | |
|---|---|---|---|---|---|---|
|  | Control | Konjac Mannan | Control | Konjac Mannan | Control | Konjac Mannan |
| Lactobacilli | $10^9$ | $10^3$ | $10^8$ | $10^3$ | $10^9$ | $10^6$ |
| Enterococci | $10^8$ | $10^2$ | $10^6$ | $10^2$ | $10^9$ | $10^6$ |
| Bacteroid | −[1] | − | − | − | $10^9$ | $10^6$ |
| Escherichia |  |  |  |  |  |  |

TABLE V-continued

|  | Stomach | | Jejunum | | Caecum | |
| --- | --- | --- | --- | --- | --- | --- |
|  | Control | Konjac Mannan | Control | Konjac Mannan | Control | Konjac Mannan |
| coli | — | — | — | — | $10^3$ | $10^1$ |

[1] The symbol "—" in the table denotes the absence of bacteria.

Effects on Bacteria in Caecum of the Administration of the Konjac Mannan Extract to Rats Decrease in the number of bacteria in caecum after administration of various concentrations of the konjac mannan was investigated by administering solutions containing varying concentrations of konjac mannan extract to groups of 5 male Wistar rats and the results appear in Table VI below.

TABLE VI

|  | Control (0.01%) | 0.1% | 0.3% | 0.5% |
| --- | --- | --- | --- | --- |
| Lactobacilli | $3.1 \times 10^7$ | $1.5 \times 10^5$ | $1.1 \times 10^4$ | $2.6 \times 10^4$ |
| Escherichia coli | $1.6 \times 10^6$ | $6.3 \times 10^5$ | $5.5 \times 10^4$ | $1.2 \times 10^3$ |
| Aerobacter aerogenes | $1.1 \times 10^7$ | $1.4 \times 10^6$ | $8.1 \times 10^5$ | $2.8 \times 10^3$ |
| Bacteroid | $3.2 \times 10^7$ | $2.7 \times 10^6$ | $8.9 \times 10^5$ | $8.8 \times 10^4$ |
| Staphylococus pyogenes | $9.1 \times 10^7$ | $5.4 \times 10^5$ | $2.3 \times 10^4$ | $1.4 \times 10^4$ |

Effects on Fecal Bacteria of the Administration of Konjac Mannan Extract to Rats Decrease in the number of fecal bacteria in rats after administration of the konjac mannan extract was investigated. It was found that the fecal bacteria count was decreased by administration of the konjac mannan as shown in Table VII. Although actual values are not presented for myxomycetes and *Pseudomonas aeruginosa*, after administration of the konjac mannan, these bacteria were not detected.

TABLE VII

|  | Control | Konjac Mannan |
| --- | --- | --- |
| Lactobacilli | $10^{6}$ [1] | $10^{5}$ [1] |
| Enterococci | $10^6$ | $10^4$ |
| Escherichia coli | $10^7$ | $10^3$ |
| Aerobacter aerogenes | $10^2$ | $10^7$ |

TABLE VII-continued

|  | Control | Konjac Mannan |
| --- | --- | --- |
| Myxomycetes | + [2] | — |
| Pseudomonas aeruginosa | + | — |

[1] Average for 5 male Wistar rats weighing around 150 g.
[2] + indicates presence; — indicates absence

Figure 2:
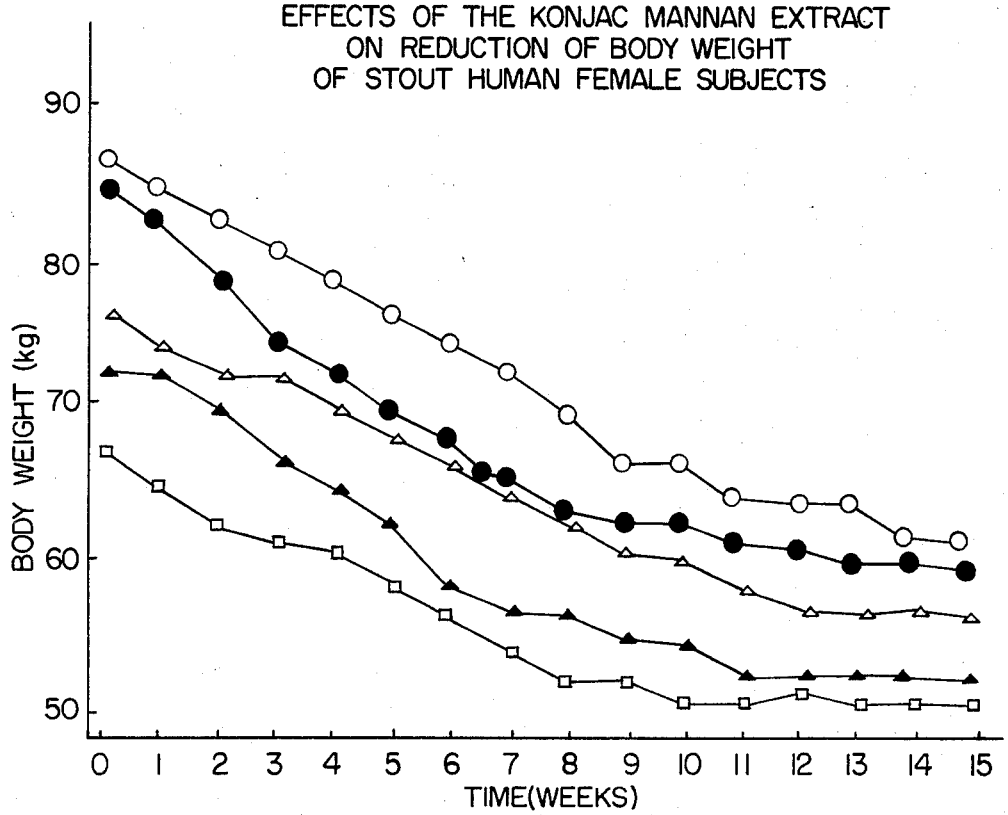

Effects on Body Weight, Blood Pressure, Blood Carbohydrates, and Cholesterol Levels of Stout Humans of Administering Konjac Mannan Extract 100 ml. of 1% aqueous solution of the konjac mannan extract of this invention were administered once a day to five stout males and five stout females for a period of 15 weeks. Body weights were measured at weekly intervals and the results are plotted for the group of males in FIG. 1 and for the group of females in FIG. 2. Blood pressure, blood carbohydrat and cholesterol levels were also observed at the end of 4, 7, and 11 weeks of such administration and the observed levels, together with the starting levels, are set forth in the following Table VIII for the males and Table IX for the females.

During this period of this test, the subjects were fed a normal rice diet which is considered the general diet in Japanese homes.

TABLE VIII

Changes in blood pressure, blood carbohydrate and cholesterol level of human males during administration of the konjac mannan extract

| Age | Height |  |  | Before administr. | 4 weeks after administr. | 7 weeks after administr. | 11 weeks after administr. |
| --- | --- | --- | --- | --- | --- | --- | --- |
| 50 | 170 cm | Blood Pres. | max. | 172 | 170 | 160 | 160 |
|  |  |  | min. | 110 | 110 | 110 | 110 |
|  | ○ | Blood carbohyd. |  | 140 | 120 | 120 | 110 |
|  |  | Cholesterol |  | 300 | 280 | 270 | 250 |
| 47 | 169 cm | Blood pres. | max. | 190 | 182 | 175 | 170 |
|  |  |  | min. | 130 | 130 | 125 | 120 |
|  | ▲ | Blood carbohyd. |  | 145 | 140 | 138 | 122 |
|  |  | Cholesterol |  | 350 | 325 | 300 | 285 |
| 51 | 163 cm | Blood pres. | max. | 185 | 172 | 160 | 155 |
|  |  |  | min. | 122 | 120 | 115 | 110 |
|  | ● | Blood carbohyd. |  | 140 | 130 | 123 | 115 |
|  |  | Cholesterol |  | 380 | 355 | 334 | 300 |
| 51 | 161 cm | Blood pres. | max. | 175 | 175 | 170 | 170 |
|  |  |  | min. | 122 | 120 | 115 | 115 |
|  | □ | Blood carbohyd. |  | 123 | 120 | 115 | 110 |
|  |  | Cholesterol |  | 385 | 355 | 311 | 300 |
| 46 | 155 cm | Blood pres. | max. | 172 | 172 | 173 | 172 |
|  |  |  | min. | 110 | 110 | 108 | 107 |

TABLE VIII-continued
Changes in blood pressure, blood carbohydrate and cholesterol level of human males during administration of the konjac mannan extract

| Age | Height | | Before administr. | 4 weeks after administr. | 7 weeks after administr. | 11 weeks after administr. |
|---|---|---|---|---|---|---|
|  | | Blood carbohyd. | 120 | 115 | 110 | 112 |
| | | Cholesterol | 372 | 351 | 343 | 311 |

TABLE IX
Changes in blood pressure, blood carbohydrate and cholesterol level of human females during administration of the konjac mannan extract

| Age | Height | | | Before administr. | 4 weeks after administr. | 7 weeks after administr. | 11 weeks after administr. |
|---|---|---|---|---|---|---|---|
| 60 | 147 cm ○ | Blood pres. | max. min. | 180 133 | 172 130 | 160 120 | 140 110 |
| | | Blood carbohyd. | | 234 | 200 | 185 | 170 |
| | | Cholesterol | | 420 ± 10 | 350 ± 10 | 302 | 255 |
| 61 | 152 cm ● | Blood pres. | max. min. | 192 140 | 180 135 | 172 130 | 164 125 ± 5 |
| | | Blood carbohyd. | | 200 ± 17 | 195 | 181 | 172 |
| | | Cholesterol | | 420 | 375 | 320 | 301 ± 11 |
| 57 | 152 cm △ | Blood pres. | max. min. | 180 120 | 180 120 | 170 117 | 170 117 |
| | | Blood carbohyd. | | 140 | 133 | 131 | 125 |
| | | Cholesterol | | 308 | 301 | 297 | 290 |
| 47 | 150 cm ▲ | Blood pres. | max. min. | 153 108 | 151 98 | 145 91 | 145 91 |
| | | Blood carbohyd. | | 110 | 108 | 107 | 105 |
| | | Cholesterol | | 285 | 286 | 287 | 285 |
| 46 | 155 cm □ | Blood pres. | max. min. | 155 108 | 145 98 | 135 91 | 135 91 |
| | | Blood carbohyd. | | 110 | 100 | 105 | 101 |
| | | Cholesterol | | 281 | 275 | 272 | 257 |

What is claimed is:

1. A method for reducing body weight in overweight Japanese humans fed with the general Japanese diet which comprises orally administering a therapeutically effective dose of purified, water-soluble konjac mannan in the range of about 0.1 – 10 g. per kg of body weight per day.

2. The method of claim 1 wherein said konjac mannan is obtained by extracting with water the ground tuber of the konjac plant, dialyzing such extract against water and lyophilizing the thus dialyzed extract to remove water.

3. The method of claim 1 wherein said dose is in the range of about 0.1 – 1 gm per kg of body weight.

* * * * *